(12) United States Patent
Kim

(10) Patent No.: US 12,740,005 B2
(45) Date of Patent: Sep. 15, 2026

(54) ELECTROMAGNETIC FIELD OUTPUT HANDLE UNIT FOR ELECTROMAGNETIC THERAPY DEVICE USING THERMAL MANAGEMENT FUNCTION

(71) Applicant: K1MED GLOBAL INC., Seoul (KR)

(72) Inventor: Sangsik Kim, Seoul (KR)

(73) Assignee: K1MED GLOBAL INC., Seoul (KR)

( * ) Notice: Subject to any disclaimer, the term of this patent is extended or adjusted under 35 U.S.C. 154(b) by 433 days.

(21) Appl. No.: 18/437,283

(22) Filed: Feb. 9, 2024

(65) Prior Publication Data

US 2024/0306342 A1 Sep. 12, 2024

Related U.S. Application Data

(63) Continuation of application No. PCT/KR2023/004802, filed on Apr. 10, 2023.

(30) Foreign Application Priority Data

Mar. 10, 2023 (KR) ........................ 10-2023-0032056

(51) Int. Cl.
*A61N 2/02* (2006.01)
*H05K 7/20* (2006.01)

(52) U.S. Cl.
CPC ........... *H05K 7/20172* (2013.01); *A61N 2/02* (2013.01)

(58) Field of Classification Search
CPC . A61N 2/00–12; H05K 7/20172; H01F 27/28
See application file for complete search history.

(56) References Cited

U.S. PATENT DOCUMENTS

2001/0012912 A1 8/2001 Feucht
2016/0030763 A1* 2/2016 Midorikawa ............ A61N 2/02 600/13
2019/0115144 A1 4/2019 Park et al.
2023/0285767 A1* 9/2023 Kim ........................ A61N 2/02
(Continued)

FOREIGN PATENT DOCUMENTS

KR 10-2003-0065126 A 8/2003
KR 10-0556230 B1 3/2006
(Continued)

OTHER PUBLICATIONS

International Search Report for PCT/KR2023/004802 mailed Dec. 4, 2023 from Korean Intellectual Property Office.

*Primary Examiner* — Kaylee R Wilson
(74) *Attorney, Agent, or Firm* — Revolution IP, PLLC

(57) ABSTRACT

An electromagnetic field output handle unit for an electromagnetic therapy device using a thermal management function, includes: a fan cover unit that has a cylindrical structure with a fan mounting space that is opened to a front side thereof; an air supply fan unit that is provided inside the fan mounting space provided inside the fan cover unit; a cover fixing unit that is formed in a plate shape connected to a front end part of the fan cover unit; a bobbin unit of a cylindrical shape that is connected to a front end part of the cover fixing unit; a coil unit that is wound over a predetermined area of an outer circumferential surface of the bobbin unit; and a bobbin cover unit that has a cylindrical structure with a bobbin cover space that is opened to a rear side thereof.

9 Claims, 5 Drawing Sheets

(56) References Cited

U.S. PATENT DOCUMENTS

2025/0065141 A1* 2/2025 Song ........................ H01F 27/28
2025/0387637 A1* 12/2025 Yoon ...................... A61N 2/006

FOREIGN PATENT DOCUMENTS

KR 10-0810606 B1 3/2008
KR 10-1022244 B1 3/2011
KR 10-1891480 B1 9/2018
KR 10-2411063 B1 6/2022

* cited by examiner

ELECTROMAGNETIC FIELD OUTPUT HANDLE UNIT FOR ELECTROMAGNETIC THERAPY DEVICE USING THERMAL MANAGEMENT FUNCTION

CROSS REFERENCE TO RELATED APPLICATIONS

This application is a Continuation of PCT International Patent Application No. PCT/KR2023/004802 filed on Apr. 10, 2023, which claims priority to Korean Patent Application No. 10-2023-0032056 filed on Mar. 10, 2023 which are all hereby incorporated by reference in their entirety.

BACKGROUND OF THE INVENTION

The present invention relates to an electromagnetic field output handle unit for an electromagnetic therapy device using a thermal management function.

An electromagnetic therapy device provides stimulation therapy using the principle that when a magnetic field is applied to a human body, a new electric field is generated to generate current through electromagnetic induction, and ions electrically stimulate surrounding nerves.

In a case where the current is rapidly changed momentarily in a coil provided in such an electromagnetic therapy device, a magnetic field is generated on a main surface of the coil, and a larger time-varying magnetic field is induced by a magnetic core. The time-varying magnetic field generates eddy current in a conductor.

By using a method of stimulating nerves by inducing current passing through a membrane of nerve fibers by change in the magnetic field to cause depolarization of a membrane potential, the magnetic field passes through the body and generates an electric field within the body, which is related to occurrence of ion flow due to a potential difference.

Since such stimulation by the magnetic field has an advantage in that the intensity of the electric field induced during entering the skin is reduced by a much lower level compared with electrical stimulation, it is possible to stimulate nerves located deeply in the body compared with the electrical stimulation. Further, for the same effect, since the intensity of the stimulation applied to the skin is low, the degree of discomfort or pain of a patient that is a treatment target is relatively low.

In electromagnetic field therapy devices that provide the above-mentioned advantages, various structural and functional modifications have been attempted to expand a treatment range or increase a treatment efficiency. In this regard, "ELECTROMAGNETIC EXTRACORPOREAL SHOCK WAVE THERAPY DEVICE USING DISK-SHAPED COIL" disclosed in Korean Patent Registration No. 10-2411063 (hereinafter, referred to as 'the prior art') provides a technique capable of solving a problem of a low energy concentration rate due to a shockwave dispersing structure.

However, in the case of conventional electromagnetic therapy devices including the prior art, since the degree of improvement in the energy concentration rate in relation to generation of a magnetic field that directly affects a treatment efficiency is low, there is a restriction in a coil mounting structure, and in particular, it is difficult to efficiently manage heat generated in the magnetic field generation process.

SUMMARY OF THE INVENTION

The present invention has been made in view of the above problems, and it is an object of the present invention to provide an electromagnetic field output handle unit for an electromagnetic therapy device using a thermal management function, capable of improving an energy concentration rate, efficiently utilizing a mounting space a coil that plays a practical role in generating a magnetic field, and efficiently managing heat generated due to generation of a magnetic field around the coil.

In order to achieve the above and other objects, according to an aspect of the present invention, there is provided an electromagnetic field output handle unit for an electromagnetic therapy device using a thermal management function, including: a fan cover unit that has a cylindrical structure with a fan mounting space that is opened to a front side thereof, is formed with a plurality of air discharge holes that communicate with the fan mounting space on a side surface thereof, and is formed with at least one air intake hole that communicates with the fan mounting space on a rear side thereof; an air supply fan unit that is provided inside the fan mounting space provided inside the fan cover unit to suction outside air through the air intake hole through fan operation and discharge the suctioned air through a discharge port provided in a front part thereof; a cover fixing unit that is formed in a plate shape connected to a front end part of the fan cover unit, is formed with a first open hole through which a front end part of the air supply fan unit is inserted to cover the air discharge port at a central part thereof, and is formed with at least one second open hole that is opened front and back to communicate with the fan mounting space around the first open hole; a bobbin unit of a cylindrical shape that is connected to a front end part of the cover fixing unit, and is formed with an air moving hole; a coil unit that is wound over a predetermined area of an outer circumferential surface of the bobbin unit to form a plurality of coil parts in a front-back direction and a plurality of coil layers in a radial direction; and a bobbin cover unit that has a cylindrical structure with a bobbin cover space that is opened to a rear side thereof, is connected to the front end part of the cover fixing unit to cover the bobbin unit and the coil unit provided in the bobbin cover space.

Here, the coil unit may include a cable with a rectangular cross-sectional shape.

Further, the coil unit may include a conductor assembly in which a plurality of conductor wires are arranged to be twisted along a cross-sectional direction, and an insulator made of polytetrafluoroethylene (PTFE) that shields the plurality of conductor assemblies to form the cable with the rectangular cross-sectional shape.

In addition, the number of the conductor assemblies in the coil unit may be 2 to 5, and each conductor assembly may be formed by twisting 100 to 250 conductor wires, the conductor wire that forms the conductor assembly may have a diameter of 0.05 mm to 0.10 mm, and the conductor assembly of the coil unit has a total cross-sectional area of 4 $mm^2$ to 8 $mm^2$.

The rectangular cross-section of the insulator of the coil unit may have a thickness of 2 mm to 3 mm and a width of 7 mm to 9 mm.

Further, the bobbin unit may include: a bobbin connecting part that is connected to the front end part of the cover fixing unit at a position inside the at least one second open hole formed at the front end part of the cover fixing unit, and is formed with a rear-end region of the air moving hole that communicates with the discharge port of the air supply fan unit; a coil connecting part that is recessed from the bobbin connecting part to form a predetermined L-shaped step and to have a narrowed diameter, and extends forward, on which the coil unit is wound; and a bobbin front end part that forms a coil support jaw with an expanded diameter compared with the coil connecting part and having a predetermined L-shaped cross section, and is formed with a front-end region of the air moving hole that communicates with the bobbin cover space of the bobbin cover unit.

In addition, the coil unit may be wound over the outer surface of the coil connecting part to form 3 to 6 coil parts in the front-back direction and 3 to 5 coil layers in the radial direction.

Further, during moving to the front-end region of the air moving hole formed inside the bobbin front end part, the air may be discharged toward the bobbin cover space of the bobbin cover unit and may spread outward to flow into the space between the outside of the bobbin unit and the inside of the bobbin cover unit through the at least one second open hole formed in the cover fixing unit.

Furthermore, the coil connecting part may be formed with a plurality of third open holes that are opened in the radial direction and have a predetermined size so that a part of the inner surface of the coil unit wound on the coil connecting part is exposed toward the air moving hole.

According to the present invention, the following effects are achieved.

First, it is possible to improve an energy concentration rate and achieve efficient space use for a mounting structure of the coil that practically affects generation of a magnetic field through the coil unit having a rectangular cross-sectional shape.

Second, by suctioning outside air and using it to manage the effect of temperature rise due to generation of a magnetic field around the bobbin where the coil is wound, it is possible to effectively solve various problems due to heat generated by a magnetic field.

Third, by effectively forming a movement path from internal suction of outside air to external discharge and having a structure that allows heat exchange through contact both inside and outside the coil during air movement, it is possible to effectively manage heat generated by a magnetic field.

BRIEF DESCRIPTION OF DRAWINGS

The above and other objects, features and other advantages of the present invention will be more clearly understood from the following detailed description taken in conjunction with the accompanying drawings, in which.

DETAILED DESCRIPTION OF THE INVENTION

Preferred embodiments of the present invention will be described in more detail with reference to the attached drawings, but description of well-known technical parts will be omitted or simplified for ease of explanation.

Figure 1:
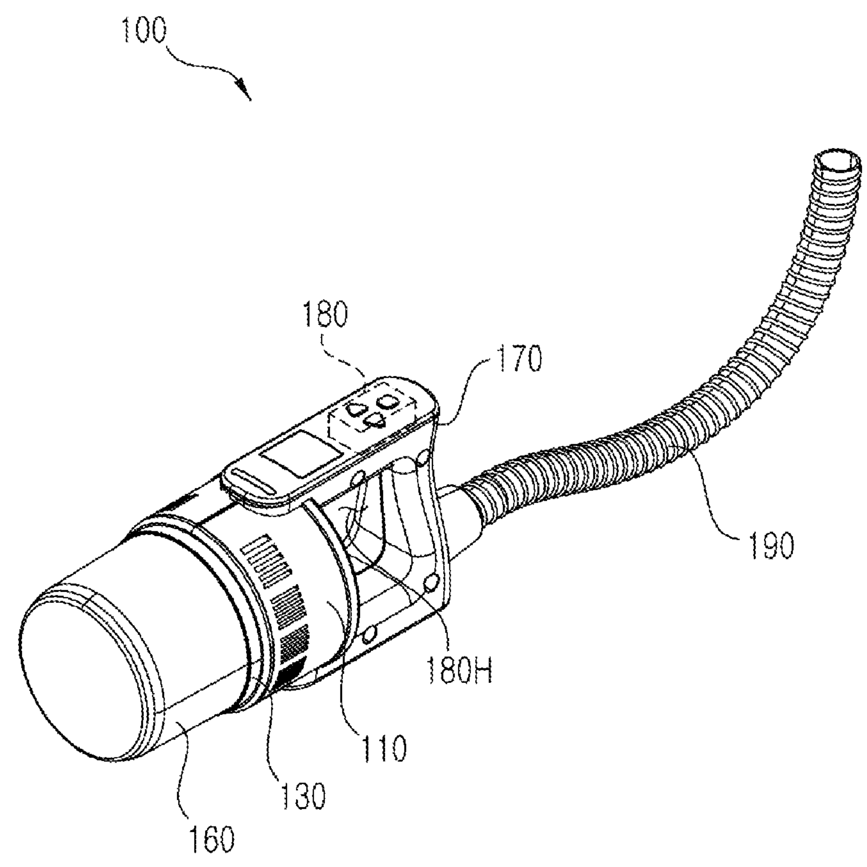
FIG. 1 is a perspective view showing an electromagnetic field output handle unit for an electromagnetic therapy device according to an embodiment of the present invention.
Figure 2:
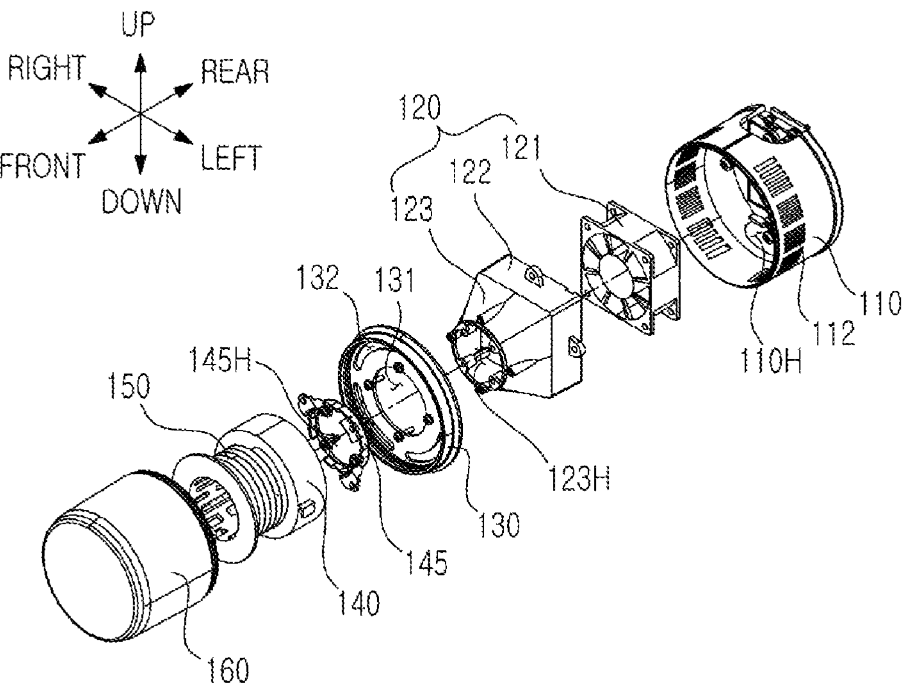
FIG. 2 is an exploded perspective view showing a detailed configuration of the electromagnetic field output handle unit for the electromagnetic therapy device according to the embodiment of the present invention.

Referring to FIGS. 1 and 2, an electromagnetic field output handle unit 100 for an electromagnetic therapy device according to an embodiment of the present invention includes a fan cover unit 110, an air supply fan unit 120, a cover fixing unit 130, a bobbin unit 140, a coil unit 150, a bobbin cover unit 160, a handle unit 170, a controller 180, and a hose unit 190, in order to improve an energy concentration rate and use efficiency in coil-based magnetic field output and effectively manage heat generated during operation.

The fan cover unit 110 has a cylindrical structure with a fan mounting space 110H that is opened to a front side thereof, and the air supply fan unit 120 (which will be described later) is accommodated in the fan mounting space 110H.

As shown in FIG. 1, the handle unit 170 is coupled to a rear side of the fan cover unit 110 to provide a predetermined grip space (170H) that allows gripping of a user who performs treatment using the electromagnetic field output handle unit 100 for the electromagnetic therapy device according to the present embodiment.

Inside the handle unit 170, the controller 180 for controlling application of an electric signal for generating a magnetic field to the coil unit 150 (which will be described later) and driving of the air supply fan unit 120.

Further, the hose unit 190 is connected to a rear side of the handle unit 170, in which a cable for electrical connection with a main body (not shown) of the electromagnetic therapy device is provided.

Figure 3:
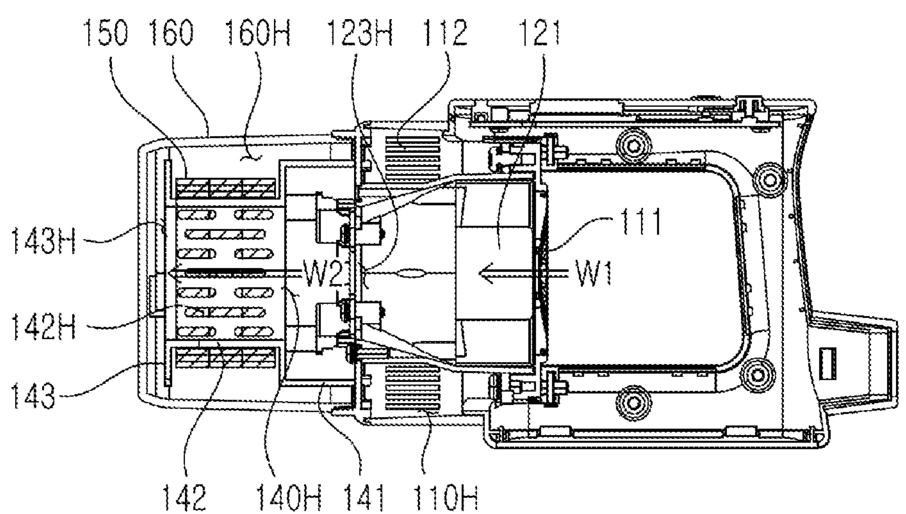
FIG. 3 is a sectional view showing the detailed configuration of the electromagnetic field output handle unit for the electromagnetic therapy device according to the embodiment of the present invention.

As shown in FIG. 2, a plurality of air discharge holes 112 that communicate with the fan mounting space 110H are provided on a side surface of the fan cover unit 110, and as shown in FIGS. 2 and 3, at least one air intake hole 111 that communicates with the fan mounting space 110H is formed on a rear surface thereof, which are used for heat management using outside air.

More specifically, the at least one air intake hole 111 formed on the rear surface of the fan cover unit 110 moves outside air toward the fan mounting space 110H to be suctioned into the air supply fan unit 120 provided in the fan mounting space 110H, and the plurality of air discharge holes 112 formed on the side surface of the fan cover unit 110 discharge air that has performed heat exchange by performing the heat management function to the outside.

The air supply fan unit 120 is mounted inside the fan mounting space 110H provided inside the fan cover unit 110 by a mounting frame of a fan fixing part 122 in which a fan module 121 is mounted. Here, when the air supply fan unit 120 is operated, outside air is suctioned through the air intake hole 111 by fan rotation of the fan module 121, and the suctioned air is discharged through a discharge port 123H provided in a front part thereof.

Specifically, the air moved in through the air intake hole 111 from the outside is suctioned through the fan module 121, is collected by an air collecting part 123 connected to a front end part of the fan fixing part 122 provided as a structure whose cross-sectional area narrows toward the front end part thereof, is discharged through the discharge port 123H, and passes through an air moving hole 140H formed inside the bobbin unit 140 (which will be described later), as shown in FIG. 3.

The cover fixing unit 130 has a plate shape connected to a front end part of the fan cover unit 110 at a rear end part thereof, and is connected to the bobbin unit 140 and the bobbin cover unit 160 (which will be described later) at a front end part thereof.

As shown in FIG. 2, the cover fixing unit 130 has, at a central part thereof, a first open hole 131 that is formed to surround the discharge port 123H in a state where the front end part of the air collecting part 123 of the air supply fan unit 120 is inserted therein.

In addition, the cover fixing unit 130 has at least one second open hole 132 that is opened in a front-back direction to communicate with the fan mounting space 110H of the fan cover unit 110 and is formed around the first open hole 131 formed at the central part of the cover fixing unit 130.

Here, in a state where the first open hole 131 formed at the central part of the cover fixing unit 130 and the second open hole 132 formed around the first open hole 131 are spaced apart from each other, the bobbin unit 140 is connected to a plate-shaped space between the first open hole 131 and the second open hole 132, and the bobbin cover unit 160 is connected to a plate-shaped space outside the second open hole 132.

In this configuration, the first open hole 131 allows the discharge port 123H of the air collecting part 123 to be directly connected to the air moving hole 140H provided inside the bobbin unit 140 (which will be described later), and the second open hole 132 allows a space between the inside of the bobbin cover unit 160 and the outside of the bobbin unit 140 to be directly connected to the open area of the fan mounting space 110H of the fan cover unit 110.

The bobbin unit 140 has a cylindrical shape formed with the air moving hole 140H, and is connected to the front end part of the cover fixing unit 130 through a plate-shaped bobbin fixing part 145 formed with a central hole 145H.

As described above, the bobbin unit 140 is provided so that the first open hole 131 provided at the central part of the cover fixing unit 130 and the at least one second open hole 132 provided outside the first open hole 131 are spaced from each other in a radial direction to form peripheral areas.

Further, the bobbin unit 140 is configured so that the coil unit 150 is wound over a certain area thereof and forms a magnetic field when an electric signal is applied to the coil unit 150.

To this end, the bobbin unit 140 has a basic structure in which a bobbin connecting part 141, a coil connecting part 142, and a bobbin front end part 143 are integrated.

Figure 4:
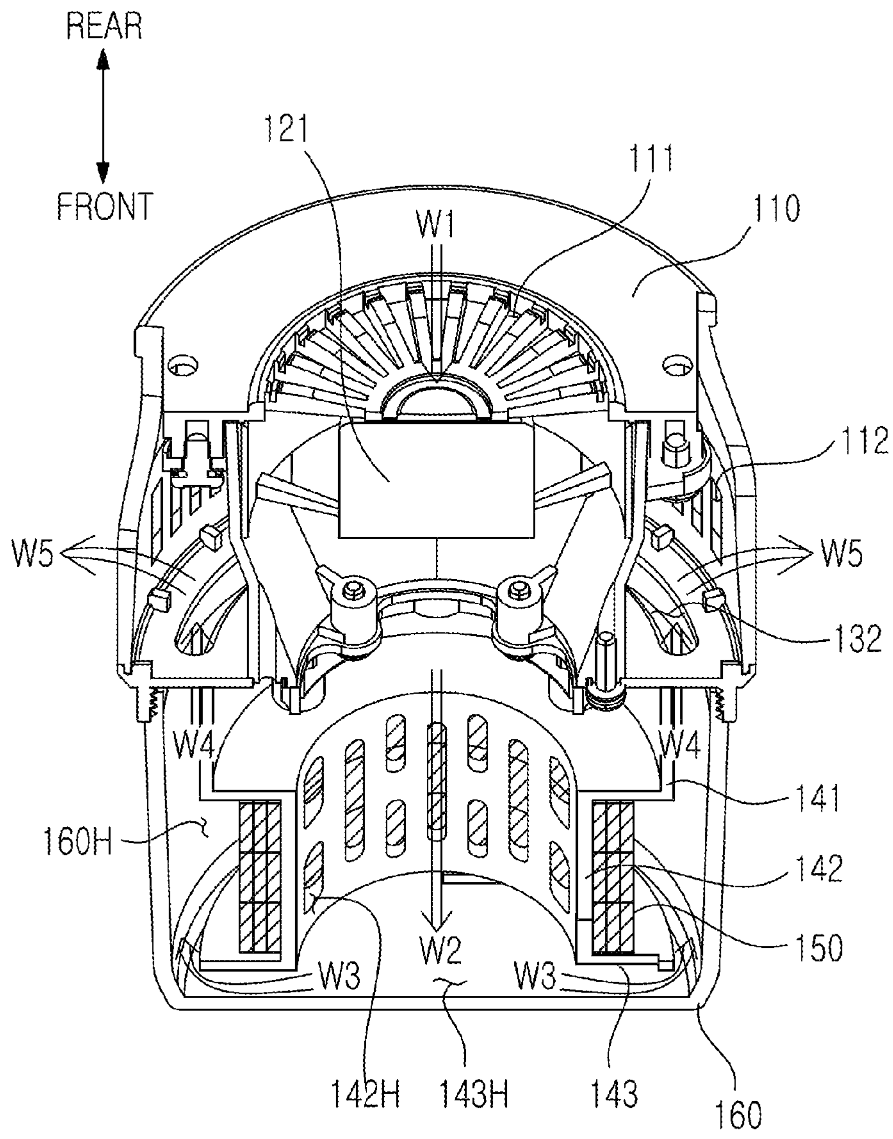
FIG. 4 is a sectional perspective view showing the detailed configuration of the electromagnetic field output handle unit for the electromagnetic therapy device according to the embodiment of the present invention.

Here, as shown in FIGS. 3 and 4, the bobbin connecting part 141 is connected to the space between the outside of the first open hole 131 formed at the front end part of the cover fixing unit 130 and the inside of the at least one second open hole 132 through the bobbin fixing part 145, in which a rear-end region of the air moving hole 140H that communicates with the discharge port 123H of the air supply fan unit 120 is positioned at a front end part thereof.

Then, as shown in FIGS. 3 and 4, the coil connecting part 142 is recessed from the bobbin connecting part 141 to form a predetermined L-shaped step and to have a narrowed diameter, and extends forward.

The coil unit 150 (which will be described later) is wound on an outer surface of the coil connecting part 142 to generate a magnetic field through application of an electric signal.

Here, as shown in FIGS. 3 and 4, the coil connecting part 142 is formed with a plurality of side open holes 142H that are opened in the radial direction and have a predetermined size so that a part of the inner surface of the coil unit 150 wound on the coil connecting part 142 is exposed toward the air moving hole 140H.

Further, as shown in FIGS. 3 and 4, the bobbin front end part 143 forms a coil support jaw with an expanded diameter compared with the coil connecting part 142 and having a predetermined L-shaped cross section.

The bobbin front end part 143 is provided with a front-end region 143H of the air moving hole 140H that communicates with a bobbin cover space 160H of the bobbin cover unit 160.

The coil unit 150 is wound over a predetermined area 142 of the outer circumferential surface of the bobbin unit 140 to form a plurality of coil parts in the front-back direction and a plurality of coil layers in the radial direction, and electrically connected to a main body through the controller 180 to generate a magnetic field on the basis of application of an electric signal.

Figure 5:
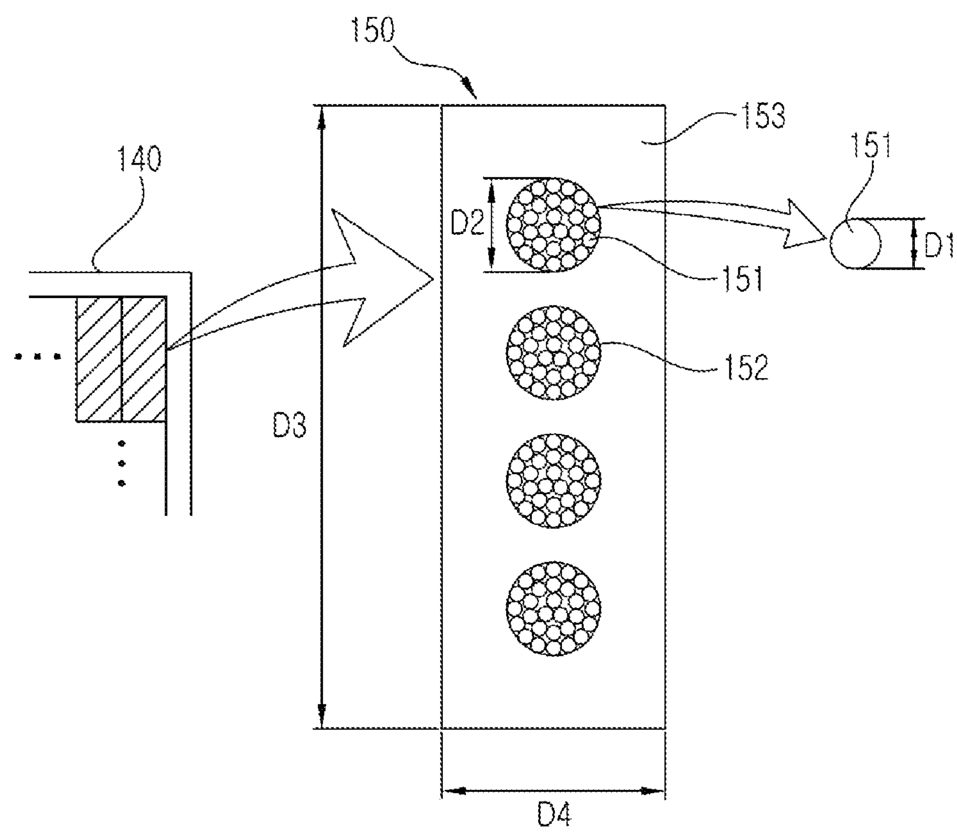
FIG. 5 is a diagram showing a detailed configuration of a coil unit in the electromagnetic field output handle unit for the electromagnetic therapy device according to the embodiment of the present invention.

As shown in FIG. 5, the coil unit 150 is preferably provided as a cable with a rectangular cross-sectional shape, to thereby make it possible to improve an energy concentration rate and achieve efficient space use for a mounting structure of the coil that practically affects generation of a magnetic field.

In a conventional configuration in which a magnetic field is generated by a cylindrical coil, there is a limitation in improving the energy concentration rate, and further, there is a problem in that it is difficult to achieve efficient space use due to a large unnecessary space in a mounting structure.

Specifically, in order to provide the cable having the rectangular cross-sectional shape as shown in FIG. 5, the coil unit 150 has a configuration in which a plurality of conductor wires 151 are arranged to be twisted along a cross-sectional direction to form a conductor assembly 152, the plurality of conductor assemblies 152 are arranged in the radial direction to be spaced from each other, and an insulator 153 made of polytetrafluoroethylene (PTFE) shields the plurality of conductor assemblies 152.

Here, polytetrafluoroethylene (PTFE) that forms the insulator 153 that shields the plurality of conductor assemblies 152 is preferably a material of Teflon (trademark).

In addition, the number of the conductor assemblies 152 in the coil unit 150 is 2 to 5 (preferably, 4 as shown in FIG. 5), and each conductor assembly 152 is formed by twisting 100 to 250 (preferably, 215) conductor wires 151.

Further, each of the conductor wires 151 that forms the conductor assembly 152 has a diameter (D1) of 0.05 mm to 0.10 mm (preferably, 0.08 mm), and is covered by an insulator made of polyurethane.

As a result, the conductor assembly 152 of the coil unit 150 has a total cross-sectional area ($(0.5\times D2)^2\times 3.14\times 4$ in FIG. 5) of 4 $mm^2$ to 8 $mm^2$ (preferably, 4.3 $mm^2$), the rectangular cross-section of the insulator 153 for covering all the conductor assemblies 152 has a thickness (D4) of 2 mm to 3 mm (preferably, 2.4±0.2 mm) and a width (D3) of 7 mm to 9 mm (preferably, 8.1±0.2 mm).

The coil unit 150 having the above-mentioned structural and functional features is wound over the outer surface of the coil connecting part 142 of the bobbin unit 140 to form 3 to 6 coil parts in the front-back direction and 3 to 5 coil layers in the radial direction.

The bobbin cover unit 160 has a cylindrical structure with a bobbin cover space 160H that is opened to a rear part thereof, and is connected to the front end part of the cover fixing unit 130 to cover the bobbin unit 140 and the coil unit 150 in the bobbin cover space 160H.

During use, an outer surface of the bobbin cover unit 160 substantially contacts or is positioned close to the skin of a patient that is a treatment target.

In the configuration in which the coil unit 150 having the above-described features is wound on the outer surface of the coil connecting part 142 of the bobbin unit 140, since a contact area of the coil unit 150 becomes wide to reduce space loss, in a case where an electric signal is applied to generate a magnetic field, the energy concentration rate increases, but a large amount of heat may be generated. To solve this problem, the respective components form an air moving path for heat management in their structures and connections.

As shown in FIGS. 3 and 4, air moved in through the air intake hole 111 from the outside is suctioned (W1) by the fan module 121, is collected by the air collecting part 123 and is discharged through the discharge port 123H toward the front part thereof, and is then moved (W2) to the air moving hole 140H formed inside the bobbin unit 140.

Here, the air (W2) passing through the air moving hole 140H formed inside the bobbin unit 140 directly contacts with the coil unit 150 through the plurality of third open holes 142H formed in the coil connecting part 142 of the bobbin unit 140 on which the coil unit 150 is wound to perform cooling through heat exchange.

Then, as shown in FIG. 4, during moving to the front-end region of the air moving hole 140H provided inside the bobbin front end part 143, the air is discharged toward the bobbin cover space 160H of the bobbin cover unit 160 and spreads outward (W3) to flow into the space between the outside of the bobbin unit 140 and the inside of the bobbin cover unit 160.

Then, the air flowing into the space between the outside of the bobbin unit 140 and the inside of the bobbin cover unit 160 contacts the outside of the coil unit 150 wound around the coil connecting part 142 of the bobbin unit 140 to perform cooling through heat exchange, and immediately moves (W4) into the fan mounting space 110H of the fan cover unit 110 through at least one second open hole 132 provided in the cover fixing unit 130.

Then, the air moved to the fan mounting space 110H of the fan cover unit 110 is discharged (W5) to the outside through the plurality of air discharge holes 112 connected thereto. By repeating the above-described cycle, it is possible to continuously perform heat management.

The above-described embodiments are not intended to limit but illustrate the technical idea of the present invention, and the scope of the technical idea of the present invention is not limited by these exemplary embodiments. The scope of protection of the present invention should be interpreted by claims below, and all technical ideas within an equivalent scope should be interpreted as being included in the scope of the invention.

The invention claimed is:

1. An electromagnetic field output handle unit for an electromagnetic therapy device using a thermal management function, comprising:

- a fan cover unit that has a cylindrical structure with a fan mounting space that is opened to a front side thereof, is formed with a plurality of air discharge holes that communicate with the fan mounting space on a side surface thereof, and is formed with at least one air intake hole that communicates with the fan mounting space on a rear side thereof;
- an air supply fan unit that is provided inside the fan mounting space provided inside the fan cover unit to suction outside air through the air intake hole through fan operation and discharge the suctioned air through a discharge port provided in a front part thereof;
- a cover fixing unit that is formed in a plate shape connected to a front end part of the fan cover unit, is formed with a first open hole through which a front end part of the air supply fan unit is inserted to cover the air discharge port at a central part thereof, and is formed with at least one second open hole that is opened front and back to communicate with the fan mounting space around the first open hole;
- a bobbin unit of a cylindrical shape that is connected to a front end part of the cover fixing unit, and is formed with an air moving hole;
- a coil unit that is wound over a predetermined area of an outer circumferential surface of the bobbin unit to form a plurality of coil parts in a front-back direction and a plurality of coil layers in a radial direction; and
- a bobbin cover unit that has a cylindrical structure with a bobbin cover space that is opened to a rear side thereof, is connected to the front end part of the cover fixing unit to cover the bobbin unit and the coil unit provided in the bobbin cover space.

2. The electromagnetic field output handle unit according to claim 1, wherein the coil unit includes a cable with a rectangular cross-sectional shape.

3. The electromagnetic field output handle unit according to claim 2, wherein the coil unit includes:

- a conductor assembly in which a plurality of conductor wires are arranged to be twisted along a cross-sectional direction; and
- an insulator made of polytetrafluoroethylene (PTFE) that shields the plurality of conductor assemblies to form the cable with the rectangular cross-sectional shape.

4. The electromagnetic field output handle unit according to claim 3, wherein the number of the conductor assemblies in the coil unit is 2 to 5, and each conductor assembly is formed by twisting 100 to 250 conductor wires, the conductor wire that forms the conductor assembly has a diameter of 0.05 mm to 0.10 mm, and the conductor assembly of the coil unit has a total cross-sectional area of 4 $mm^2$ to 8 $mm^2$.

5. The electromagnetic field output handle unit according to claim 4, wherein the rectangular cross-section of the insulator of the coil unit has a thickness of 2 mm to 3 mm and a width of 7 mm to 9 mm.

6. The electromagnetic field output handle unit according to claim 2, wherein the bobbin unit includes:

- a bobbin connecting part that is connected to the front end part of the cover fixing unit at a position inside the at least one second open hole formed at the front end part of the cover fixing unit, and is formed with a rear-end region of the air moving hole that communicates with the discharge port of the air supply fan unit;
- a coil connecting part that is recessed from the bobbin connecting part to form a predetermined L-shaped step and to have a narrowed diameter, and extends forward, on which the coil unit is wound; and
- a bobbin front end part that forms a coil support jaw with an expanded diameter compared with the coil connecting part and having a predetermined L-shaped cross section, and is formed with a front-end region of the air moving hole that communicates with the bobbin cover space of the bobbin cover unit.

7. The electromagnetic field output handle unit according to claim 6, wherein the coil unit is wound over the outer surface of the coil connecting part to form 3 to 6 coil parts in the front-back direction and 3 to 5 coil layers in the radial direction.

8. The electromagnetic field output handle unit according to claim 6, wherein during moving to the front-end region of the air moving hole formed inside the bobbin front end part, the air is discharged toward the bobbin cover space of the bobbin cover unit and spreads outward to flow into the space between the outside of the bobbin unit and the inside of the bobbin cover unit through the at least one second open hole formed in the cover fixing unit.

9. The electromagnetic field output handle unit according to claim 6, wherein the coil connecting part is formed with a plurality of third open holes that are opened in the radial direction and have a predetermined size so that a part of the inner surface of the coil unit wound on the coil connecting part is exposed toward the air moving hole.

* * * * *